(12) United States Patent
Pringle et al.

(10) Patent No.: US 6,837,094 B2
(45) Date of Patent: Jan. 4, 2005

(54) PORTABLE APPARATUS FOR MEASURING THE FLEXIBILITY OF A GOLF CLUB HEAD

(76) Inventors: Matthew M. Pringle, 5 Farnsworth Ave., Bordentown, NJ (US) 08505; Stephen Robert Otto, 34 Lodge Walk, Elie, Fife (GB), KY9 1DD (*) Notice: Subject to any disclaimer, the term of this patent is extended or adjusted under 35 U.S.C. 154(b) by 42 days.

(21) Appl. No.: 10/371,717

(22) Filed: Feb. 21, 2003

(65) Prior Publication Data

US 2004/0182131 A1 Sep. 23, 2004

(51) Int. Cl.[7] .................................................. G01N 3/30
(52) U.S. Cl. ..................................................... 73/12.02
(58) Field of Search ............................ 73/12.02, 12.01, 73/12.04, 12.05, 12.06, 12.09, 12.14

(56) References Cited

U.S. PATENT DOCUMENTS

| | | | | |
|---|---|---|---|---|
| 5,951,410 A | * | 9/1999 | Butler et al. ................ | 473/223 |
| 6,000,286 A | * | 12/1999 | Naruo et al. .................. | 73/491 |
| 6,505,498 B2 | * | 1/2003 | Pringle ...................... | 73/12.04 |
| 6,702,692 B1 | * | 3/2004 | Smith ......................... | 473/289 |

* cited by examiner

Primary Examiner—Max Noori
(74) Attorney, Agent, or Firm—Francis C. Hand; Carella, Byrne, Bain, et al (57) ABSTRACT

The apparatus employs a steel impact ball which is mounted in a pendulum manner to swing against the face of a golf club head. The golf club is secured at one end to a spacer block on the base of the apparatus and the head of the club is freely mounted in facing relation to the impact ball. The ball is pivoted from a fixed position to impact against the head of the golf club and an oscilloscope is used to record et acceleration and movement of the ball after impact of the ball on the club face and also calculates a velocity history of the face of the ball. The time at which the calculated velocity is at a maximum is determined. Several impacts may be made to obtain a number of calculated times and the relative flexibility of the golf dub head is estimated in accordance with the equation:

$$B = i_c - A \frac{1}{V_m^k}$$

A simpler procedure may also be employed using a single velocity (with one or more than one impact). In this instance, the relative flexibility of the golf dub head is estimate in accordance with the equation:

$$B = t_c.$$

19 Claims, 6 Drawing Sheets

PORTABLE APPARATUS FOR MEASURING THE FLEXIBILITY OF A GOLF CLUB HEAD

This invention relates to a portable apparatus for measuring the flexibility of a golf club head. More particularly, this invention relates to a portable apparatus and method of determining a relative measure of the flexibility of a head of a golf club.

Rule 5a, Appendix II, of the Rules of Golf requires that the material and construction of the face or a golf club head not have the effect, at impact of a spring or impart significantly more spin to a ball than a standard steel face, or have any other effect which would unduly influence the movement of the ball Heretofore, various techniques have been employed to determine the effect at impact of a golf dub head on a ball. One such procedure has been published by the United States Golf Association, Procedure for Measuring the Velocity Ratio of a Club Head for Conformance to Rule 5a, Appendix II, Revision 2, Feb. 8, 1999. The procedure, however, requires several steps and is relatively time consuming.

U.S. Pat. No. 6,505,498 describes a relatively simple and efficient apparatus and method for determining a representative spring constant of a golf club head.

It is an object of this invention to provide a portable apparatus for measuring the flexibility of a golf club head and in particular to determine a relative measure of flexibility of a club head.

It is another object of the invention to provide a portable version of the apparatus described in U.S. Pat. No. 6,505,498.

Briefly, the invention provides an apparatus for measuring the flexibility a golf club head as well as a method of determining a relative measure of the flexibility of a golf club head wherein a golf club head is held stationary and a mass of material is impacted against the face of the head.

The apparatus comprises means for fixedly positioning a golf club (either with a permanent or removable shaft or the like) having a head thereon with a face of the head in a predetermined plane and means for positioning a mass of material at a fixed point for freely pivoting of the mass of material in a plane perpendicular to the predetermined plane and about a pivot point to impact the mass of material against the face of the golf dub.

The means for positioning the golf dub includes a clamp for securing the shaft of the golf club in a firm manner. The clamp includes a means for accurately adjusting the horizontal position of the golf club.

The means for positioning the mass of material includes a tower having the mass of material pivotally mounted thereon. The tower also includes two rails on which the vertical position of the pivoting mount may be adjusted. Combining the horizontal adjustability of the club clamp and the vertical adjustability allows for full adjustability of the mass impact point.

The apparatus also has a means for recording the acceleration of the mass in the direction of its movement.

The means for recording an acceleration typically includes an accelerometer connected to a recording device via a wire for producing a voltage signal in dependence on an acceleration of the mass in the direction of its movement and the means for recording includes an oscilloscope connected to the accelerometer to receive and record the voltage signal and to calculate the velocity history.

In one embodiment, the apparatus is constructed with a base on which a block is mounted on one end with a clamp mounted on the block for securing the shaft of a golf club in place.

In addition, a head block is mounted in the tower in vertically adjustable relation and carries a shaft that is pivotally mounted on and depends from the head block for pivoting about a pivot point in a plane perpendicular to the fixed plane in which the club face is disposed.

The mass of material is mounted on the end of the shaft for impacting against the face of club head. In this embodiment, an axle is mounted in depending relation from the head block and has the shaft secured to and depending therefrom.

A means is also provided for releasably holding the mass of material in several positions spaced from the face of the golf club head. For example, this means includes a ratchet and pawl assembly for releasably holding the axle in one of several selected positions against the weight of the mass of material whereby upon release of the ratchet and pawl assembly the mass of material is free to pivot under gravity towards the fixed plane.

The method of measuring the relative flexibility of a golf club head in accordance with the invention requires the mounting of a head of a golf club with a face thereof in a predetermined plane and the impacting of a mass of material against the face of the golf club head. In accordance with the invention, an acceleration of said mass of material in the direction of its movement after impact with said face of said head is determined and recorded to obtain an acceleration signal. Next, the acceleration signal is integrated to determine velocity over time.

A maximum velocity ($V_m$) is then determined from the integrated signal and a characteristic time $t_c$ is calculated from integrated signal from the formula:

$$t_c = t_e - t_s.$$

wherein $t_e$ is the end time when the velocity reaches a predetermined fraction of the maximum velocity and $t_s$ is the start time when the velocity reaches a lesser predetermined fraction of the maximum velocity.

A value B is then determined from the expression:

$$B = t_c - A \frac{1}{V_m^k}$$

wherein B is a measure of the relative flexibility of the golf dub head and A indicates the sensitivity of said characteristic time to impact velocity in dependence on the elastic modulus of the face of the golf club head.

In one embodiment, the head of a golf club is mounted with a face thereof in a predetermined plane and a suspended mass of material is freely pivoted under gravity about a pivot point in a plane perpendicular to the predetermined plane of the club face to impact against the face of the golf club head.

Initially, the golf club face is first marked in a consistent location, preferably the geometric center of the face. This will serve as the desired impact location. In order to aim the pivoting mass, a lower, vertically adjustable block on the tower rails is equipped with a hole. A removable hollow cylinder is equipped with two pins in the front the cylinder is positioned into the hole in the lower block with a groove such that the two pins are vertical. These two pins are used to ensure that the face of the club is vertical. A laser pointer (or any other convenient pointing device) is then fitted into the hollow cylinder such that the laser light shines on the face of the club. The horizontal adjustment of the clamp and vertical adjustment of the lower block are then used to shine the laser light on the impact spot marked on the face of the club. The lower block is locked down with a thumbscrew located on the left of the block.

Having positioned the lower block, a spacer on one of the rails is slid into position which also positions the vertically adjustable head block. The spacer length is such that, having positioned the lower block on the impact spot, the pivotally mounted mass will then strike the impact spot the spacer is locked into position with a thumbscrew (which also positions the head block) and then the lower block is lowered out of the way.

The ratchet is equipped with a multitude of release positions, preferably three but may be more or as few as one. The procedure is such that the operator raises the mass to the highest release position, releases the mass and the acceleration is captured by the oscilloscope. This procedure may or may not be repeated multiple times. The mass may be then raised to the next lowest position (if multiple release heights are desired) and the procedure is repeated until all positions have been used.

The electronics of the apparatus, namely, the accelerometer, oscilloscope and computer to carry out the calculations to measure the flexibility of the golf club.

These and other objects and advantages of the invention will become more apparent from the following detailed description taken in conjunction with the accompany drawings wherein

FIG. 7 shows a typical velocity profile with the characteristic time associated with the profile; and Referring to FIG. 1, the apparatus for measuring the flexibility of a golf club head, such as a head of a driver, is constructed to be manually portable. To this end, the apparatus 10 is constructed so as to be manually lifted by one or two persons and moved onto a table top or the like. In addition, the apparatus 10 is constructed so as to be readily taken apart for transportation purposes and put together again in a simple manner without the need for tools.

Figure 1:
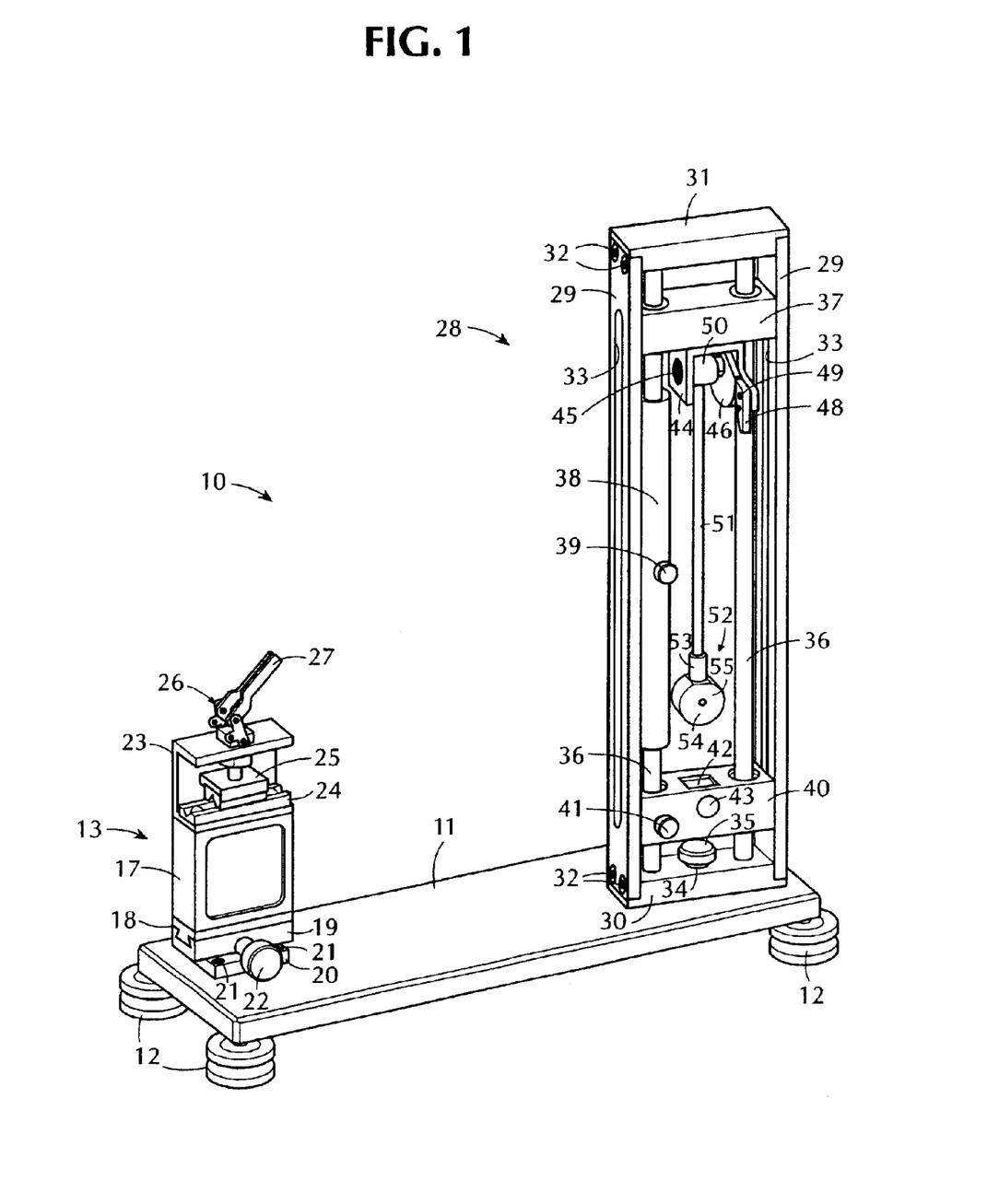
FIG. 1 illustrates a perspective view of a portable apparatus constructed in accordance with the invention.

As illustrated, the apparatus 10 includes a base 11 constituted by a rectangular plate that is supported at each of four corners by a leveling foot 12. For example, each foot 12 has a threaded stem which can be threaded into a bore (not shown) in the underside of the base 11. Each foot 12 also has a flat bottom for resting on a flat surface (not shown). Rotation of a foot 12 relative to the base 11 allows for a leveling of the base 11 into a true horizontal plane.

The base 10 also has a mounting means 13 for fixedly positioning a golf club 14 (see FIG. 2) having a head 15 with a face 16 of the head 15 in a fixed vertical plane perpendicular to the plane of the base 11.

The mounting means 13 includes a spacer block 17 that is secured to a slide plate 18 that, in turn, is slidably mounted in a guide 19 via a dove-tail arrangement. The guide 19 is, in turn, fixedly mounted on a plate 20 secured, as by screws 21 to the base 11. A thumbscrew 22 is threaded into the guide 19 in order to abut the slide plate 18 and lock the guide plate 18 in position. Thumbscrew 22 is used to adjust the horizontal position of slide plate 18.

The spacer block 17 carriers a clamp bracket 23 of U-shape cross section. One leg of this clamp bracket 23 has a shaft clamp pad 24 secured thereon. The opposite leg supports a second shaft clamp pad 25 via a clamping mechanism 26 that is actuated by a lever 27. The clamping mechanism may also be actuated by a screw system, cam or other suitable means. Rotating the lever 27 in one direction causes the shaft clamp pad 25 to move towards the opposite clamp pad 24 and vice versa. As illustrated, each of the clamp pads 24, 25 is provided with a V-shaped recess for clamping the handle of a golf club 14 (see FIG. 2) therebetween. The details of the clamping mechanism are otherwise conventional and need not be further described.

In order to disassemble the mounting means, the spacer block 17 guide plate 18 may be slid off the guide 19 as a unit.

The apparatus 10 also includes means for positioning a mass of material at a fixed point for freely pivoting of the mass of material in a plane perpendicular to the plane of the face 16 of the club head 15 and about a pivot point to impact against the face 16 of the club head 15. To this end, the apparatus 10 has a tower 28 that can be readily mounted on the base 11 in a fixed upright manner.

The tower 28 includes a pair of vertically disposed rails 29 which are secured at the bottom to a lower tower mount 30 and at the top to an upper tower mount 31 as by screws 32. Each tower rail 29 is provided with an elongated slot 33.

The lower tower mount 30 is provided with a central bore 34 through which a thumb screw 35 passes vertically into threaded engagement with the base 11. The tightening of the thumb screw 35 serves to secure the tower 28 relative to the base 11 about a vertical axis passing through the axis of the thumb screw 35.

The tower 28 is rotated about its vertical axis by an angle of 8½° relative to a longitudinal axis of the base 11. This angle represents an average loft angle for drivers.

The tower 28 also includes a pair of shafts 36 that extend between the lower and upper tower mounts 30, 31. In this respect, each shaft 36 fins into a suitably sized bore in the respective tower mounts 30.31.

A head block 37 is slidably mounted on the pair of shafts 36 to be freely movable vertically along the shafts 36. In addition, a sleeve 38 is slidably mounted on one of the shafts 36 and is held in place by a threaded screw 39 which is threaded into the sleeve 38 to abut against the shaft 36 in order to lock the sleeve 38 relative to the shaft 36.

A further black 40 is slidably mounted on the tower shafts 36 below the sleeve 38. This block 40 is secured to one of the shafts 36 by means of a screw 41 which is threaded into the block 40 to abut the shaft 36 that carries the sleeve 38.

Figure 2:
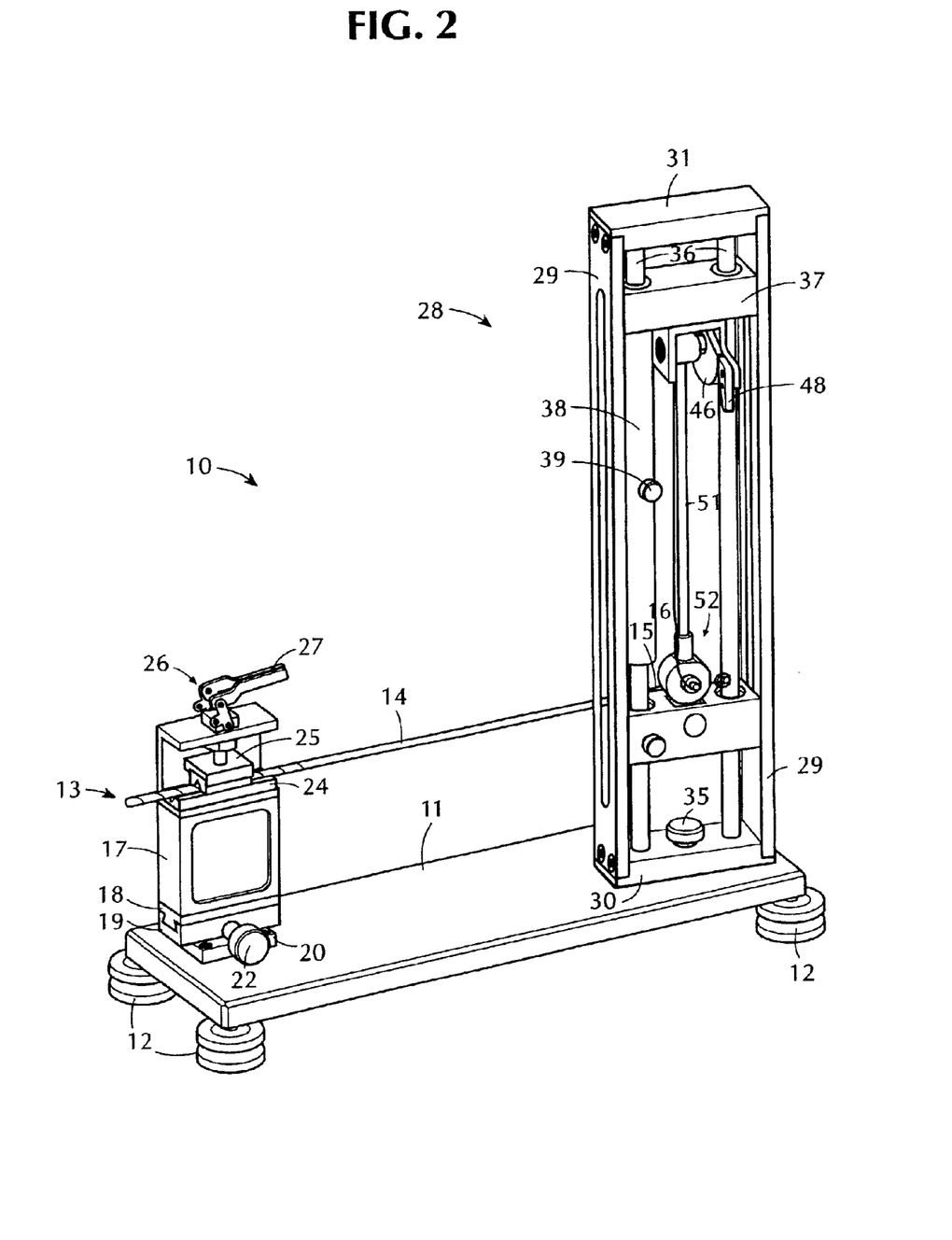
FIG. 2 illustrates a perspective view of the apparatus of FIG. 1 with a golf club mounted therein at the initiation of a test procedure.

The block 40 includes a recess 42 in the upper surface to receive the mass of material 52 for the purpose of locking the mass in place for transportation as indicated in FIG. 2. In addition, the block 40 has a bore 43 for receiving a laser pointer (not shown).

Figure 4A:
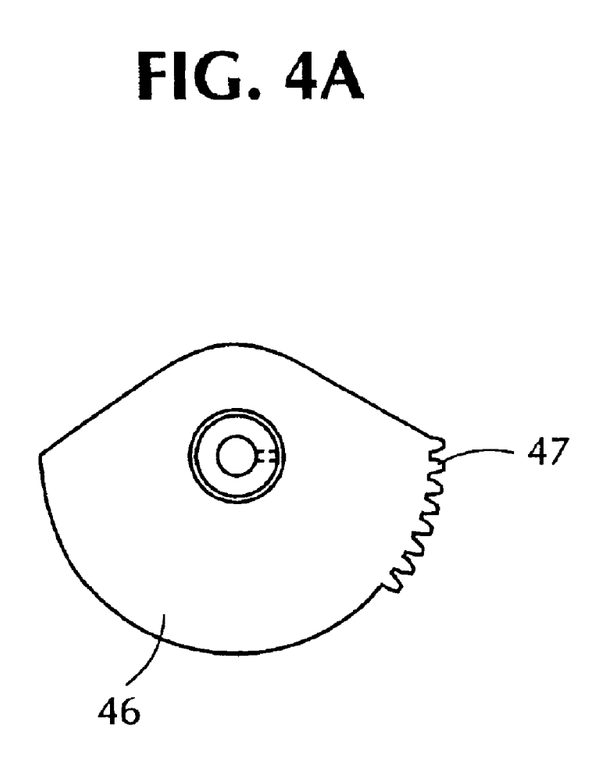
FIG. 4A illustrates a ratchet employed in a means for positioning the mass material at a fixed point.
Figure 4B:
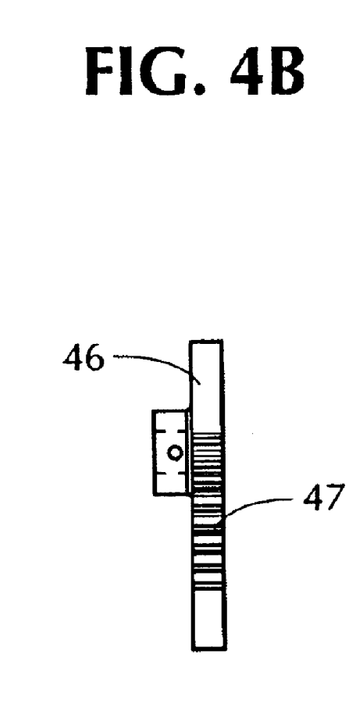
FIG. 4B illustrates a side view of the ratchet.

The head block 37 carries a U-shaped clevis 44 in depending relation. In this respect, the clevis 44 is secured to the underside of the head block 37 by means of two screws (not shown). The clevis 44, in turn, carries an axle 45 on which a ratchet gear 46 is fixedly carried. As indicated in FIGS. 4A and 4B, the ratchet gear 46 has a toothed segment 47 on one side.

The clevis 44 also carries a ratchet pawl 48 which is pivotally mounted thereon via a pin 49. This ratchet pawl 48 includes a tooth for engaging between the teeth of the toothed segment 47 of the ratchet gear 46 in order to prevent rotation of the axle 45. The ratchet pawl 48 may be positioned between any two teeth of the toothed segment 47 of the ratchet gear 46 in order to fix the axle 45 in different angular positions relative to a horizontal axis passing through the axle 45. The pawl 48 is manually actuated so that pivoting of the pawl 48 on the pin 49 allows the pawl 48 to disengage from the toothed segment 47 of the gear 46 thereby allowing the axle 45 to rotate freely under gravity.

As illustrated, a hub 50 is carried on the axle 45 to rotate therewith. Any suitable means (not shown) may be used to secure the hub 50 to the axle 45 for this function.

A shaft 51 is secured as by bonding with epoxy into the hub 50 and depends therefrom. The shaft 51, in turn, carries a mass of material 52 in pendulum-like fashion at the lower end. This mass of material 52 includes a hosel 53 for receiving the shaft 51 in secured relation. In addition, the mass of material 52 includes an impact ball 54 which is secured to the hosel 53 in a fixed manner. For example, where the hosel 53 is made of aluminum, the impact ball 54 is made of hardened tool steel and is secured to the hosel 53 as by an epoxy. The face (not shown) of the impact ball is spherical to correspond to the face of a golf ball. In addition, the backside of the impact ball 54 has a threaded bore 55 an accelerometer 56 (see FIG. 2).

Referring to FIG. 2, wherein like reference characters indicate like parts as above, in order to measure the flexibility of a golf club head, the golf 14 is positioned so that the club head 15 is positioned behind the tower 28 and in the path of the impact ball 55.

Initially, the golf club face is first marked in a consistent location, preferably the geometric center of the face. This will serve as the desired impact location. In order to aim the impact ball 55, a removable hollow cylinder (not shown) is slid into the bore 43 in the lower, vertically adjustable block 40 on the tower shafts 36. This removable hollow cylinder is equipped with two pins (not shown) in the front The cylinder is positioned into the bore 43 in the lower block 40 with a groove such that the two pins are vertical. These two pins are used to ensure that the face 16 of the club 14 is vertical.

A laser pointer (not shown) is then fitted into the hollow cylinder such that a laser light from the pointer shines perpendicularly onto the face 16 of the club 14. The horizontal adjustment of the spacer block 17 and vertical adjustment of the lower block 40 are then used to shine the laser light on the impact spot marked on the face 16 of the club 14. The lower block 40 is then locked down with the thumb screw 41 located on the left of the block.

The screw 39 is then loosened to allow the sleeve 38 to be slid down the shaft 36 onto the block 40 and then tightened. During this time, the head block 37 also slides downwardly with the sleeve 38 thereby moving the impact ball 55 into alignment with the face 16 of the club head 15, and, particularly into alignment with the center of the club face 16, i.e. the spot marked on the face of the club head as shown in FIG. 3.

If not previously connected, an accelerometer 56 is connected to the backside of the impact ball 54 e.g. by being threaded into the bore 55 in the ball 54 in order to determine the acceleration of the ball 54 in the direction of its motion during impact with the dub head face suitable wiring connects the accelerometer 58 to an digital storage oscilloscope (not shown) to deliver signals corresponding to the determined accelerations signals to the oscilloscope that, in turn, records the determined acceleration and calculates a velocity history of the ball 54 over time.

A computer (not shown) is also connected to the oscilloscope in order to store and process the data.

Figure 3:
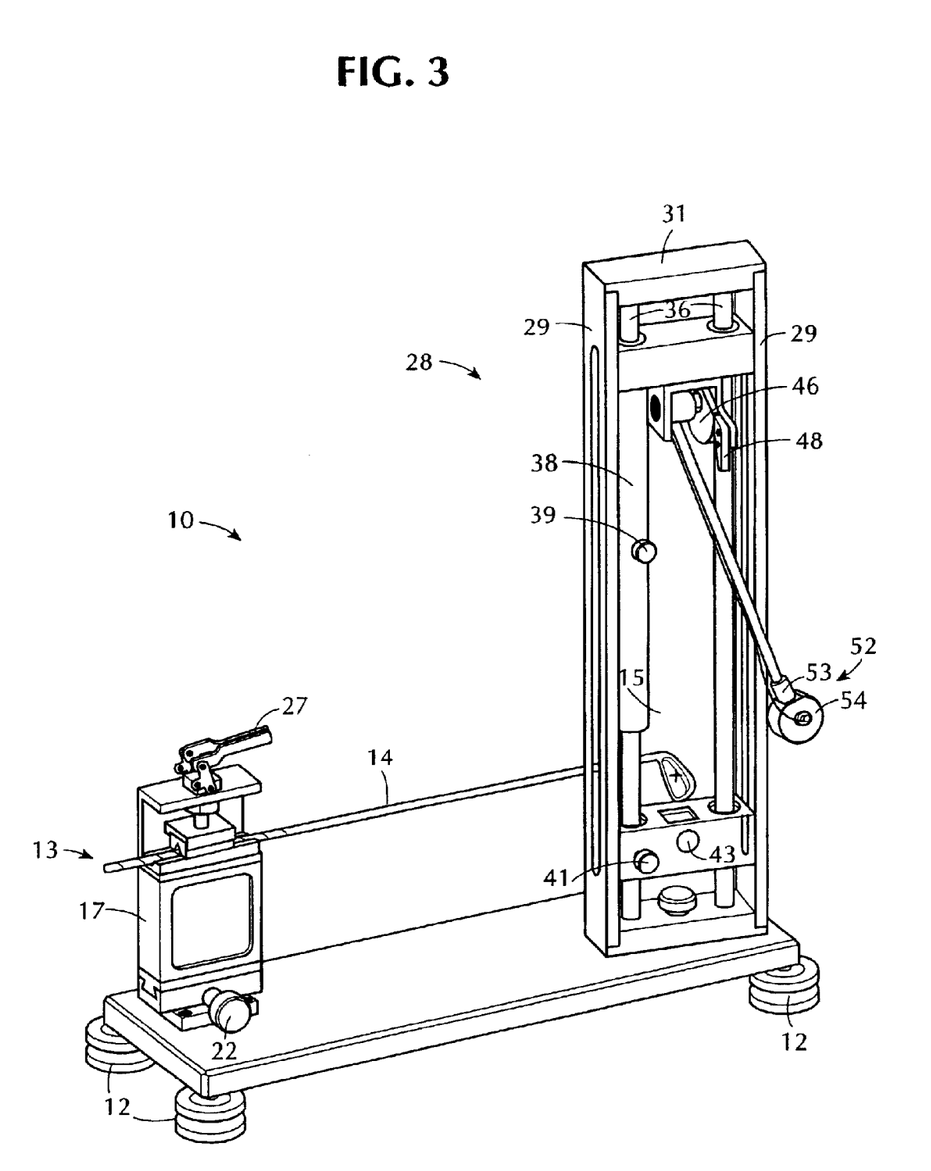
FIG. 3 illustrates a view similar to FIG. 2 with the apparatus during a test period.

Next, the impact ball 55 is moved away from the golf club head 15, for example into a position as shown in FIG. 3 and locked in place via the ratchet gear 46 and pawl 48. In this respect, the pawl 48 may be used to lock the impact ball 55 in any angular position relative to the golf club.

Next, the pawl 48 is manually pivoted so as to release the ratchet gear 46. This allows the impact ball 55 to swing freely under gravity to impact against the face 16 of the golf club 14. (See FIG. 2).

After impact of the impact ball 54 on the face 16 of the golf dub 15, the ball rebounds and moves away from the golf club face 16. The oscilloscope 56 connected in place records the acceleration of the impact ball 54. At the same time, the oscilloscope or any suitable device calculates a velocity history of the impact ball 54.

Figure 5:
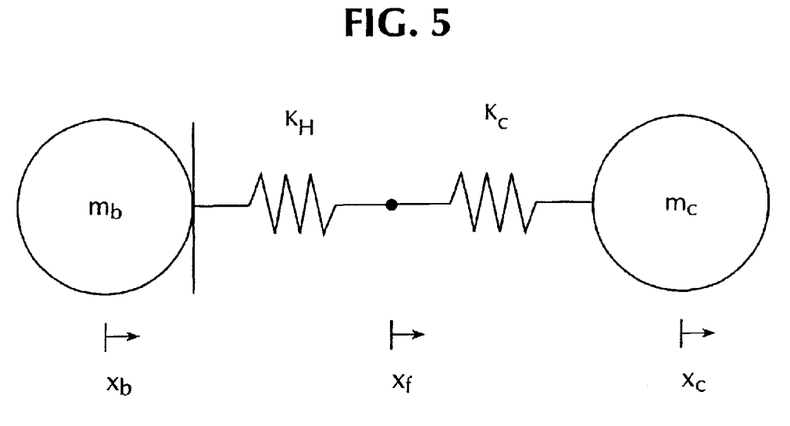
FIG. 5 illustrates a model of the impact between the club and the mass.

Referring to FIG. 5, the analytical dynamic model of the club-ball interaction is illustrated with the mass of the impact ball 54 represented by $M_b$ and the mass of the golf dub by $M_c$.

Figure 6:
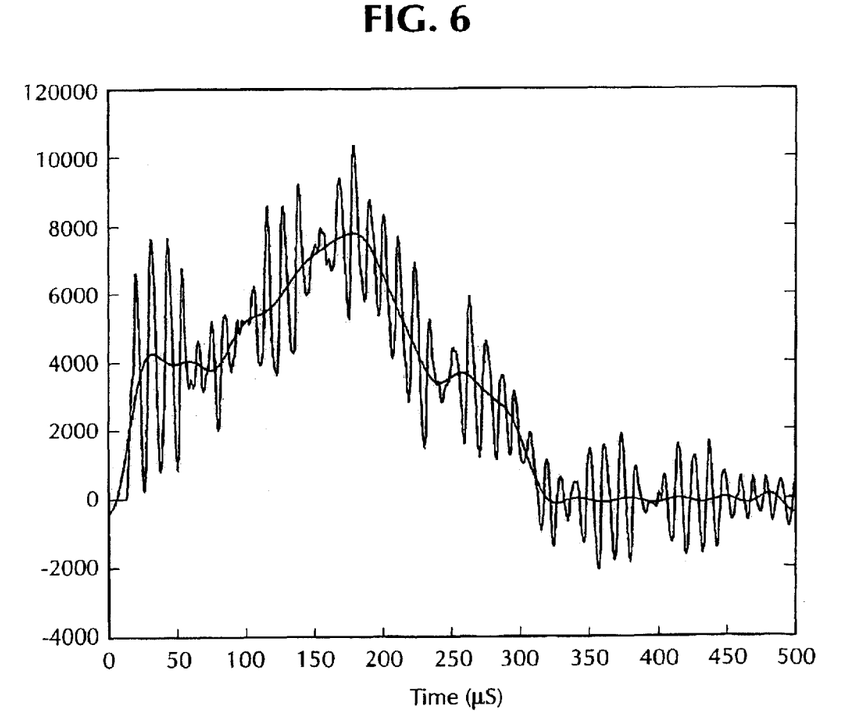
FIG. 6 illustrates a sample of an unfiltered and a filtered signal.

The acceleration signal, due to its noise is first filtered in order to isolate the true signal. Any number of filters, both analog or digital may be employed to reduce or remove the noise. In the current embodiment, a truncated Fourier Series representation of the signal is used with all components above 30 kHz eliminated. A sample of an unfiltered and a filtered signal is provided in FIG. 6.

Figure 7:
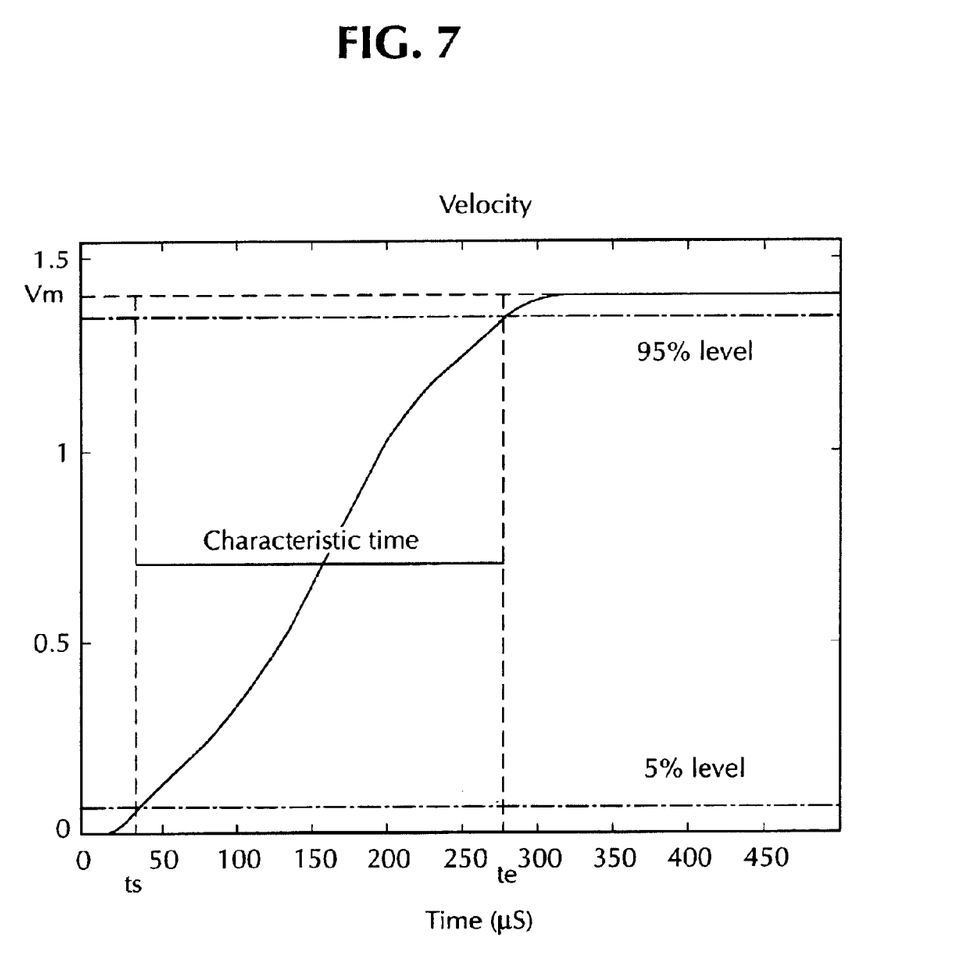

The filtered signal is then integrated to find velocity. This may be achieved numerically or in the case of the Fourier Series representation of acceleration, analytically. The maximum velocity ($V_m$) is found from the integrated signal. The start time ($t_s$) is then defined as the time when the velocity reaches X % of the maximum velocity. X may range from 0 to 99% of maximum velocity. The end time ($t_e$) is defined as the time when the velocity reaches Y % of the maximum velocity. Y may range from 1 to 100%. Preferably in this procedure X=5% and Y=95% of maximum velocity. FIG. 7 shows a typical velocity profile with the characteristic time associated therewith. The characteristic time is calculated as $t_c = t_e - t_s$. This procedure is repeated for each impact such that there is a series of data points having horizontal coordinates of $t_c$ and vertical co-ordinates of $V_m$, i.e.:

A model of the impact between the club and the mass is shown in FIG. 5. The club is assumed to be comprised of a mass ($m_c$), a club stiffness ($k_c$) and a non-linear spring ($k_H$) representing the Hertzian contact between the club face and the mass.

The equations of motion for this system are:

$$m_b \ddot{x}_b = k_H(x_f - x_b)$$

$$m_c \ddot{x}_c = k_c(x_f - x_c)$$

with the kinematic constraint:

$$k_H(x_b - x_f) = k_c(x_f - x_c)$$

the definition of $k_H$:

$$k_H = \tfrac{4}{3} R^{1/2} E (x_b - x_f)^{1/2}$$

Where:

$$R = \frac{1}{\frac{1}{R_b} + \frac{1}{R_c}} \quad E = \frac{1}{\frac{1-v_b^2}{E_b} - \frac{1-v_c^2}{E_c}}$$

Where R is the radius of curvature, v is the Poisson's Ratio and E the elastic modulus.

In order to evaluate the flexibility of the club from the experimental data, it is necessary to isolate the influence of the local Hertz contact flexibility. The model above was studied numerically and it has been shown that as $V_m$ approaches infinity, the effect of the Hertz contact becomes negligible. The model also shows that the relationship between characteristic time and $V_m$ may be expressed as:

$$t_c = A \frac{1}{V_m^k} + B$$

where k may range from −10 to 10, preferably k may range from 0.2 to 0.32.

The set of experimental data discussed above may be fit to this equation using a least squares minimization of error to find A and B. For positive k, it should be noted that B represents the characteristic time for $V_m = \infty$. Therefore, B is used as a relative indicator of flexibility of the club head. The value A indicates the sensitivity of characteristic time to impact velocity and is highly dependant on the face material elastic modulus.

The value B may be expressed as:

$$B = t_c - A \frac{1}{V_m^k}$$

Other forms of equations relating B, $t_c$, $V_m^k$ would also be suitable.

Typically, the value B is in microseconds ($\mu$s) and ranges from 0 to 1000. The lower the value, the stiffer the golf club. Hence, obtaining a value B of 150 $\mu$s means that this club is stiffer than a club testing out at a value B of 200 $\mu$s.

The value A typically ranges from −50 to 500 and depends on the material of the club.

In some instances, with metallic clubs for example, a more efficient test may conducted by assuming a priori that the value of A is zero and hence the test need only be conducted at a single velocity using one impact or a sample of multiple impacts at the same or nearly the same velocity. In this case, the relative indicator of flexibility, B may be found directly by:

$$B = t_c$$

The invention thus provides an apparatus 10 that can be readily lifted and moved from place to place by one or two people. Further, the apparatus 10 may be easily broken down in the sense that the tower 28 may be removed from the base 11 by unthreading of the thumb screw 34. The tower 28 may then be transported separately from the base 11 if necessary. Further, the spacer block 17 may be slid off the base 11 and separately transported. The electronics used to connect the oscilloscope (not shown) to the accelerometer 56 may also be readily disconnected.

Further, the invention provides a relatively simple technique for determining a relative measure of the flexibility of a golf club head. The methodology employs a simple arrangement of an impact mass of material that can be impacted against a freely mounted dub head face and electronics for determining an acceleration of the impact mass after impact from which calculations of velocity can be plotted over time and used to obtain a measure of the flexibility (and stiffness) of the club head.

What is claimed is:

1. An apparatus for measuring the flexibility of a golf club head, said apparatus comprising means for fixedly positioning a golf club having a head thereon with a face of said head in a predetermined plane;

means for positioning a mass of material at a fixed point for freely pivoting of said mass of material in a plane perpendicular to said predetermined plane and about a pivot point to impact said mass of material against said face of said head;

means for determining an acceleration of said mass of material in the direction of its movement after impact with said face of said head; and means for recording the determined acceleration and calculating a velocity history of said mass over time.

2. An apparatus as set forth in claim 1 wherein said means for determining an acceleration includes an accelerometer for producing a voltage signal in dependence on an acceleration of said mass of material away from said face of said head from said fixed plane and said means for recording includes an oscilloscope connected to said accelerometer to receive and record said voltage signal and to calculate said velocity history.

3. An apparatus as set forth in claim 2 wherein said mass of material is of spherical shape.

4. An apparatus as set forth in claim 3 wherein said means for positioning a golf club includes a clamp for securing a shaft of a golf club therein.

5. An apparatus as set forth in claim 4 wherein said means for positioning a mass of material includes a tower having said mass of material pivotally mounted thereon.

6. An apparatus for measuring the flexibility of a golf club head, said apparatus comprising a base;

a block mounted on one end of said base;

a clamp mounted on said block for securing a shaft of a golf dub therein;

a tower mounted on said base opposite said block;

a head block mounted in said tower in vertically adjustable relation;

a shaft pivotally mounted on and depending from said head block for pivoting about a pivot point in a plane perpendicular to said fixed plane;

a mass of material mounted on an end of said shaft for impacting against a face of a golf dub head positioned below said head block;

means for determining an acceleration of said mass of material in the direction of its movement after impact with the face of the golf club head; and means for recording the determined a acceleration and calculating a velocity history of said mass over time.

7. An apparatus as set forth in claim 6 wherein said means for determining an acceleration includes an accelerometer for producing a voltage signal in dependence on an acceleration of said mass of material away from said lace of said head and said means for recording includes an oscilloscope connected to said accelerometer to receive and record said voltage signal and to calculate said velocity history.

8. An apparatus as set forth in claim 6 wherein said clamp is horizontally adjustably mounted on said block to move a golf club horizontally relative to said tower.

9. An apparatus as set forth in claim 6 wherein said mass of material has a face of spherical shape for impacting a face of a golf club head.

10. An apparatus as set forth in claim 6 which further comprises means for releasably holding said mass of material in a position spaced from the face of the golf club head.

11. An apparatus as set forth in claim 6 which further comprises an axle mounted in depending relation from said head block and having said shaft secured to and depending therefrom.

12. An apparatus as set forth in claim 11 which further comprises means for releasably holding said mass of material in a position spaced from the face of the golf dub head.

13. An apparatus as set forth in claim 12 wherein said means for releasably holding said mass of material includes a ratchet and pawl assembly for releasably holding said axle in a selected position against the weight of said mass of material whereby upon release of said ratchet and pawl assembly said mass of material is free to pivot under gravity towards said fixed plane.

14. A method of measuring the flexibility of a golf club head said method including the steps of mounting a head of a golf club with a face thereof in a predetermined plane;

impacting a mass of material against the face of the golf club head in said predetermined plane;

determining an acceleration of said mass of material in the direction of its movement after impact with said face of said head;

recording the determined acceleration to obtain an acceleration signal;

integrating said acceleration signal to determine velocity over time;

determining a maximum velocity ($V_m$) from said integrated signal;

then calculating a characteristic time $t_c$, from said integrated signal from the formula $$t_c = t_e - t_s$$

wherein: $t_e$ is the end time when the velocity reaches a predetermined fraction of said maximum velocity and $t_s$ is the start time when the velocity reaches a lesser predetermined fraction of said maximum velocity; and then determining a value B from the expression $$B = t_c - A \frac{1}{V_m^k}$$

wherein B is a measure of the relative flexibility of the golf club head and

A indicates the sensitivity of said characteristic time to impact velocity in dependence on the elastic modulus of the face of the golf club head.

15. A method as set forth in claim 14 where B ranges from 0 to 1000 milliseconds with a lower value indicating a stiffer club then a higher value.

16. A method as set forth in claim 15 wherein A ranges from −60 to 200 for a clubs of various face materials.

17. A method of measuring the flexibility of a golf club head, said method including the steps of mounting a head of a golf club with a face thereof in a predetermined plane;

suspending a mass of material for freely pivoting about a pivot point in a plane perpendicular to said plane to impact against the face of the golf club head in said predetermined plane;

pivoting the mass of material to a position to space the mass of material from the golf club head;

thereafter releasing the mass of material from said position to freely pivot under gravity to impact the mass of material against the face of to golf club head;

determining an acceleration of said mass of material in the direction of its movement after impact with said face of said head; and recording the determined acceleration and calculating a velocity history of said mass over time.

18. A method as set forth in claim 17 wherein said step of pivoting the mass of material is conducted manually.

19. An apparatus as set forth in claim 1 wherein said mass of material has a face of spherical shape for impacting a face of a golf club head.

* * * * *

UNITED STATES PATENT AND TRADEMARK OFFICE
CERTIFICATE OF CORRECTION

PATENT NO.     : 6,837,094 B2
DATED          : January 4, 2005
INVENTOR(S)    : Pringle et al.

It is certified that error appears in the above-identified patent and that said Letters Patent is hereby corrected as shown below:

Column 1,
Lines 15, 43 and 44, change "dub" to -- club --

Column 2,
Line 44, change "dub" to -- club --

Column 3,
Line 5, change "the" to -- .The --
Line 18, cancel "to"

Column 4,
Line 15, after "block 17" insert -- and --
Line 38, change "fins" to -- fits --
Line 46, change "black" to -- block --.

Column 5,
Line 24, after "the golf" insert -- club --
Line 33, after "front" insert -- . --

Column 6,
Line 17, change "dub" to -- club --

Column 7,
Line 57, change "dub" to -- club --

Column 8,
Line 46, cancel "a"
Line 51, change "lace" to -- face --

UNITED STATES PATENT AND TRADEMARK OFFICE
CERTIFICATE OF CORRECTION

PATENT NO. : 6,837,094 B2
DATED : January 4, 2005
INVENTOR(S) : Pringle et al.

It is certified that error appears in the above-identified patent and that said Letters Patent is hereby corrected as shown below:

<u>Column 10,</u>
Line 12, change "then" to -- than --

Signed and Sealed this

Twenty-fourth Day of May, 2005

JON W. DUDAS
*Director of the United States Patent and Trademark Office*